United States Patent [19]

Bradner et al.

[11] 4,112,071
[45] Sep. 5, 1978

[54] ANTIBIOTIC COMPLEX

[75] Inventors: William T. Bradner, Manlius; James A. Bush, Fayetteville; Donald E. Nettleton, Jr., Jordan, all of N.Y.

[73] Assignee: Bristol-Myers Company, New York, N.Y.

[21] Appl. No.: 832,034

[22] Filed: Sep. 9, 1977

Related U.S. Application Data

[63] Continuation-in-part of Ser. No. 758,248, Jan. 10, 1977, abandoned, which is a continuation-in-part of Ser. No. 590,994, Jun. 27, 1975, abandoned.

[51] Int. Cl.$^2$ .............................................. A61K 35/00
[52] U.S. Cl. .................................. 424/118; 195/80 R
[58] Field of Search ........................ 424/118; 195/80 R

[56] References Cited

U.S. PATENT DOCUMENTS

| | | | |
|---|---|---|---|
| 3,590,028 | 6/1971 | Arcamone et al. | 424/180 |
| 3,616,242 | 10/1971 | Belloc et al. | 195/80 |
| 3,864,480 | 2/1975 | Wang et al. | 424/120 |

OTHER PUBLICATIONS

Brazhnikova et al., J. of Antibiotics, Apr. 1974, pp. 254–259.

Primary Examiner—Jerome D. Goldberg
Attorney, Agent, or Firm—David M. Morse

[57] ABSTRACT

A novel anthracycline antibiotic complex designated herein as figaroic acid complex is produced by fermentation of Streptosporangium sp. strain C-31,751, A.T.C.C. 31129. Figaroic acid complex inhibits the growth of various microorganisms, e.g., Staphylococcus aureus, exhibits phage inducing properties and inhibits the growth of various tumors in rodents, e.g., Sarcoma 180, L-1210 lymphatic leukemia, B-16 melanoma, Walker 256 carcinosarcoma and P-388 lymphatic leukemia.

6 Claims, 2 Drawing Figures

FIG. I INFRARED SPECTRUM OF FIGAROIC ACID COMPLEX (KBr)

FIG. 1 INFRARED SPECTRUM OF FIGAROIC ACID COMPLEX (KBr)

FIG. 2 ULTRAVIOLET ABSORPTION SPECTRA OF FIGAROIC ACID COMPLEX

ANTIBIOTIC COMPLEX

CROSS-REFERENCE TO RELATED APPLICATION

This is a continuation-in-part application of co-pending application Ser. No. 758,248 filed Jan. 10, 1977 and now abandoned which in turn is a continuation-in-part application of application Ser. No. 590,994 filed June 27, 1975 and now abandoned.

BACKGROUND OF THE INVENTION (1) Field of the Invention

This invention relates to a new anthracycline antibiotic complex and to its production and recovery.

(2) Description of the prior art

A number of anthracycline glycosides have been described in the literature. Among them, daunomycin and adriamycin are particularly being watched with keen interest in the field of cancer chemotherapy and have already been applied clinically for human cancers.

Farmitalia's U.S. Pat. on adriamycin (B-106FI; 14-hydroxy-daunomycin; INN is Doxorubincin) is 3,590,028 claiming the product by structure and disclosing its direct fermentation by S. peuceticus var. caesius. Farmitalia also issued U.S. Pat. No. 3,803,124 on chemical conversion of daunomycin to adriamycin; for direct fermentation of daunomycin (as antibiotic FI 1762) by S. peuceticus see U.K. Pat. No. 1,003,383.

Farmeitalia's daunomycin (U.K. Pat. No. 1,003,383) may be the same as Rhone-Poulenc's 13057 R.P. (formerly rubidomycin and now Daunoribicin (U.K. Pat. No. 985,598; 1,188,262; 1,241,750 and see U.S. Pat. No. 3,616,242) and is "probably" identical with Ciba's danubomycin (U.S. Pat. No. 3,092,550; U.K. Pat. No. 901,830). See also U.S. Pat. No. 3,686,163 on dihydrodaunomycin.

Cinerubin A and cinerubin B are disclosed in U.K. Pat. No. 846,130 and see also U.S. Pat. No. 3,864,480 and Keller-Schierlein et al., Antimicrobial Agents and Chemotherapy, page 68 (1970) and Chemical Abstracts, 54, 1466i (1960).

The anthracycline glycoside carminomycin described in J. Antibiotics, April 1974, pages 254–259, has been reported to be active against several animal tumor systems.

For further illustrative and summary disclosures of anthracycline antibiotics see Index of Antibiotics from Actinomycetes, Hamao Umezawa, Editor-in chief, University Park Press, State College, Penn., U.S.A. (1967) as follows:

| Antibiotic | Page Number |
|---|---|
| Aklavin | 111 |
| Cinerubin A | 220 |
| Cinerubin B | 221 |
| Danubomycin | 242 |
| Daunomycin | 243 |
| Pyrromycin | 542 |
| Rhodomycin A,B | 561 |
| Rubidomycin | 574 |

The textbook Antibiotics, Volume 1, Mechanism of Action, edited by David Gottlieb and Paul D. Shaw, Springer - Verlag New York, Inc., N.Y., N.Y. (1967) at pages 190-210 contains a review by A. DiMarco entitled Daunomycin and Related Antibiotics.

Information Bulletin, No. 10, International Center of Information of Antibiotics, in collaboration with WHO, Dec., 1972, Belgium, reviews anthracyclines and their derivatives.

SUMMARY OF THE INVENTION

There is provided by the present invention a new anthracycline antibiotic complex designated herein as figaroic acid complex, said complex being prepared by cultivating a new strain of Streptosporangium designated Streptosporangium sp. strain C-31,751, A.T.C.C. No. 31129, in an aqueous nutrient medium containing assimilable sources of nitrogen and carbon under submerged aerobic conditions until a substantial amount of figaroic acid complex is produced by said organism in said culture medium and optionally recovering the figaroic acid complex from the culture medium. The invention embraces the unresolved mixture of anthracycline antibiotics designated as figaroic acid complex in dilute solution, as crude concentrates or in solid form.

DETAILED DESCRIPTION

This invention relates to a novel anthracycline antibiotic complex designated herein as figaroic acid complex and to its preparation by fermentation of a new strain of Streptosporangium designated Streptosporangium sp. strain C-31,751. The above organism was obtained from a soil sample taken from Seelyville, Indiana. A culture of the organism has been deposited without restrictions in the American Type Culture Collection, Washington, D.C., and added to its permanent collection of microorganisms as A.T.C.C. 31129.

Figaroic acid complex inhibits growth of various Gram-positive bacteria, for example, Staphylococcus aureus and Mycobacterium tuberculosis, and various protozoa and yeasts, for example, Candida albicans, Histoplasma capsulatum, Trichomonas vaginalis and Trichomonas faetus. The substance exhibits phage inducing properties and inhibits growth of various lymphatic and soild tumor systems in rodents including Sarcoma 180, L-1210 lymphatic leukemia, Walker 256 carcinosarcoma, P-388 lymphatic leukemia and B-16 melanoma. The figaroic acid complex may be used alone or in combination with other antibacterial agents to prevent the growth of, or reduce the number of, the sensitive Gram-positive bacteria, yeasts and protozoa mentioned above. It is useful in wash solutions for sanitation purposes, e.g., for washing hands and disinfecting various laboratory, dental and medical equipment or other contaminated materials and as a bacteriostatic rinse for laundered clothes. It is also useful in treating the above-mentioned tumor systems in mice and rats.

THE MICROORGANISM

The strain C-31,751 has the following morphological characterists: Scant aerial mycelium are formed. During the early growth phase, a spore chain which is short, compact and irregularly coiled appears at the tip of the sporophore. The coiled spore chain develops into a real sporangium which is spherical in shape and 4–12 $\mu$ in diameter. Most of the sporangiophores measure 5–10 $\mu$ in length. Looped or short flexuous spore chains are occasionally co-produced with the sporangia. The substrate mycelium is branched, often curved and probably non-septated. The sporangiospore is non-motile, spherical to oval in shape and 0.7–0.9 μ in size. The spore-surface structure has not yet been determined.

Table I reports the cultural properties obtained on different media, the observations being after 1–2 months culture at 28° C. The organism forms aerial mycelium slowly on sucrose-nitrate agar, inorganic salts-starch agar, yeast extractmalt extract agar and oat meal agar.

Mass color of the aerial mycelium is whitish pink to pink. Aerial mycelium was not formed on asparagine agars, typrosine agar, nutrient agar and peptoneyeast extract-iron agar.

The sporangium is formed on inorganic saltsstarch agar, yeast extract-malt extract sugar and oat meal agar. Numerous sporangia were seen on the latter two media after incubation for seven weeks at 28° C. The mass of substrate mycelium shows granular shape on macro- and microscopic observation. The principal color of the substrate mycelium is reddish orange and reddish purple on glucose-asparagine agar and yeast extract-malt extract agar, respectively. Light yellowish diffusible pigment is produced in glucose-asparagine agar and yeast extract-malt extract agar. A trace amount or no melanoid pigment is produced in tyrosine agar and peptoneyeast extract-iron agar.

The physiological characteristics and carbohydrate utilization of strain C-31,751 are shown in Tables 2 and 3, respectively. The organism reduces nitrate to nitrite in a natural organic medium but not in an inorganic medium. Like most *Micromonospora* species, it is considerably sensitive to sodium chloride. It is a mesophilic organism. Certain carbohydrates such as sucrose, raffinose, soluble starch and D-mannitol are utilized after a long lag time.

Table 2

| Physiological Characteristics Of C-31751 | | |
|---|---|---|
| Tests | Responses | Materials And Methods |
| Nitrate reduction in inorganic medium | Negative | Czapek's sucrose-nitrate broth |
| Nitrate reduction in organic medium | Strongly positive | The organic medium, recommended by Leudemann[1] |
| Gelatin liquefaction | Completely liquefied | Basal medium: Yeast extract 0.4%, malt extract 1.0 and glucose 0.4% |
| Starch hydrolysis | Weakly positive | Hayward's starch agar |
| Skim milk agar | Poor growth, weak hydrolysis | Leudemann's medium[1] |
| 10% skim milk solution | Strong coagulation and slow peptonization | |
| Melanin formation | Not produced | Tyrosine agar and peptone-yeast extract-iron agar |
| Effect of NaCl in organic medium | Moderate growth at 0 and 0.5% NaCl. Restricted at 1 and 1.5%. No growth at 2.5%. | Basal medium: Leudemann's yeast extract-starch agar[1] |
| Growth-temperature | Maximum growth at 37° C. Medial growth at 28° C. and 43° C. No growth at 15° C. and 48° C. | Yeast extract-malt extract agar: ISP No. 2 medium |

[1]Leudemann, G. H.: *Micromonospora purpureochromogenes* (Waksman and Curtis 1916) comb. nov. (Subjective Synonym: *Micromonospora fusca* Jensen 1932). Intl. J. Syst. Bacteriol. 21: 240–247, 1971.

Table 3

| Carbohydrate-utilization Of Strain C31751* | | | | | |
|---|---|---|---|---|---|
| | I** | II | | I | II |
| D(−)-Arabinose | ± | − | D(−)-Melibiose | ++[A] | +[A] |
| L(+)-Arabinose | ++ | ++ | Trehalose | ++ | ++ |
| D-Xylose | ++[A] | ++ | Raffinose | +[A] | − |
| D-Ribose | ++ | ++ | D(−)-Melezitose | − | − |
| L-Rhamnose | ++ | ++ | Soluble starch | + | ± |
| D-Glucose | ++ | ++ | Cellulose | + | ± |
| D(+)-Galactose | ++[A] | ++ | Glycerol | ++ | ++ |
| D-Fructose | + | ++ | Inositol | ++[A] | ++ |
| D-Mannose | ++ | ++ | D-Mannitol | +[A] | +[A] |
| L(−)-Sorbose | + | − | D-Sorbitol | − | − |
| Sucrose | +[A] | +[A] | Dulcitol | − | − |
| Lactose | + | + | Salicin | ± | − |

Table 1

| Cultural Characteristics Of Strain C-31751* | | | | |
|---|---|---|---|---|
| | Growth | Reverse color** | Aerial mycelium | Diffusible Pigment |
| Sucrose-nitrate agar | Scant, fine granular | Pink | Very scant, pinkish white | None |
| Glucose-asparagine agar | Moderate, granular | Strong reddish orange | None | None or light reddish yellow |
| Glycerol-asparagine agar | Scant, fine granular | Strong orange | None | None |
| Inorganic salts-starch agar | Moderate, granular | Vivid yellowish orange | Scant, whitish | None |
| Tyrosine agar | Scant, fine granular | Light, yellowish brown | None | None |
| Nutrient agar | Moderate, granular | Dull reddish purple to dark wine | None | None |
| Yeast extract-malt extract agar | Good, crenate | Dark rose to deep reddish purple | Scant, purplish pink | Light reddish yellow |
| Oat meal agar | Moderate, granular | Purplish pink to bright purple | Scant, whitish to pale pink | Purplish pink |
| Peptone-yeast extract-iron agar | Moderate, | Dark violet | None | Gold |

*Observations after 1–2 months' culture at 28° C.
**The pigment is soluble in methanol and has a pH-indicator-like property: yellowish orange at acidic and violet at alkaline pH.

Table 3-continued

| Carbohydrate-utilization Of Strain C31751* | | | | |
|---|---|---|---|---|
| | I** | II | I | II |
| Cellobiose | ++ | ++ | No sugar — | — |

*Observations after 1-2 months' culture at 28° C.
**Basal medium
I: Pridham-Gottlieb medium plus 0.1% Difco yeast extract.
II: Leudemann's organic medium, composed of 0.5% yeast extract, 0.1% CaCO$_3$, and 1.5% agar in distilled water.
A: Aerial mycelium poorly formed. No aerial mycelium on the other sugar media.

Strain C-31,751 contains meso-diaminopimelic acid (meso-DAP) as a characteristic amino acid component in the cell wall. Diagnostic carbohydrate was not present.

Summarizing the above characteristics, strain C-31,751 forms whitish pink (shell pink) aerial mycelium and spherical sporangium. The sporangiospore is not motile. The sporangiophore is short, usually less than 10 μ in length. The mass color of the substrate mycelium is orange to violet. Distinct diffusible pigment (including melanin) is not produced. Almost all of the usual carbohydrates are utilized for the growth. The cell wall of the strain contained meso-DAP but no diagnostic sugar component.

These major characteristics indicate that strain C-31,751 is a species of the genus *Streptosporangium*. According to the taxonomic classification of *Streptosporangium* species by H. Nonomura and Y. Ohara (J. Ferment. Technol. 47 (11): 701–709, 1969 and 52 (2): 71–77 (1974), sixteen species are described. Among them, eight species have pinkish aerial mycelium and short sporangiophore; they are *Streptosporangium rubrum* Potekhina 1965, *S. longisporum* Schaffer 1969, *S. roseum* Couch 1955, *S. amethystogenes* Nonomura et Ohara 1960, *S. amethystogenes* var. nonreducens Prauser et Eckerdt 1967, *S. vulgare* Nonomura et Ohara 1960, *S. pseudovulgare* Nonomura et Ohara 1969 and *S. nondiastaticum* Nonomura et Ohara 1969. Subsequently, *S. violaceochromogenes* MK-49 was added to the same species-group (Japanese Patent No. 49-42896 of April 4, 1974).

Strain C-31,751 differs from *Streptosporangium amethystogenes, S. roseum* and *S. vulgare* in its positive growth at 42° C.; from *S. longisporum* in its glubose spore; from *S. nondiastaticum* in its positive utilization of rhamnose, inositol and starch and from *S. pseudovulgare* in its positive utilization of rhamnose and inositol and its orange or reddish purple substrate mycelium. *S. violaceochromogenes* is differentiated from Strain C-31,751 in its colorless or gold substrate mycelium and its negative or doubtful utilization of inositol and rhamnose. Strain C-31,751 shares several characteristics in common with *Streptosporangium rubrum* described by L. L. Potekhina in Mikrobiologiya, 34,292 (1965) such as the aerial mass color, color of substrate mycelium, soluble pigment and sporeshape. However, the descriptions on *S. rubrum* presently available are not sufficient to make a definite conclusion about the identity of the two organisms, and strain C-31,751 will therefore be considered an undetermined species of *Streptosporangium* until further data is available.

It is to be understood that for the production of figaroic acid antibiotic complex the present invention, though described in detail with reference to the strain of *Streptosporangium* sp. strain C-31,751, A.T.C.C. 31129, is not limited to this microorganism or to microorganisms fully described by the cultural characteristics disclosed herein. It is intended that this invention also include other figaroic acid-producing strains or mutants of the said microorganism which can be produced by methods well known in the art, for example, by subjecting the novel microorganism to X-ray or ultraviolet radiation, nitrogen mustard, phage exposure and the like.

PREPARATION OF THE COMPLEX

Figaroic acid complex is produced by cultivating a figaroic acid-producing strain of *Streptosporangium* having the characteristics of A.T.C.C. 31129 or a mutant thereof under submerged aerobic conditions in an aqueous nutrient medium. The organism is grown in a nutrient medium containing an assimilable carbon source, for example an assimilable carbohydrate. Examples of preferred carbon sources include lactose, glycerol, sucrose, corn starch, glucose, mannose and fructose. When starch is used as the carbon source in the nutrient medium, anylase may be added to the broth before harvest to reduce any emulsion problems which may occur. The nutrient medium should also contain an assimilable nitrogen source such as, for example, fish meal, peptone, soybean flour, peanut meal, cotton seed meal and corn steep liquor. Nutrient inorganic salts may also be incorporated in the medium, and such salts may comprise any of the usual salts capable of providing sodium, potassium, ammonium, calcium, phosphate, sulfate, chloride, bromide, nitrate, carbonate or like ions.

Production of the figaroic acid complex can be effected at any temperature conducive to satisfactory growth of the organism, i.e., room temperature up to about 43° C., and is conveniently carried out at a temperature of around 27° C. Ordinarily optimum production is obtained after incubation periods of about 170–210 hours. The medium normally is slightly alkaline, but the exact pH may vary according to the particular media used. The fermentation may be carried out in Erlenmeyer flasks and in laboratory or industrial fermenters of various capacities. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium for large scale production of the antibiotic complex. The medium in which the vegetative inoculum is produced can be the same, as, or different from, that utilized in the tank for the production of the new complex, as long as it is such that a good growth of the microorganism is obtained.

When the fermentation is complete, the antibiotic complex is extracted from the while broth with a water-immiscible organic solvent, the organic extract is concentrated, and the solid complex is precipitated by dilution of the concentrated extract with a suitable antisolvent. Any water-immiscible organic solvent having a polarity ranging from that of methylene chloride to that of n-butanol and having a pH in the range of from about 3.5 to 8.5 may be used in the extraction step. Examples of such water-immiscible solvents include $C_4$-$C_8$ alcohols (n-butanol, sec.-butanol, amyl alcohol, hexyl alcohol), higher ketones such as methyl isobutyl ketone, chlorinated hydrocarbons such as methylene chloride and esters such as ethyl acetate. Solvents in the intermediate polarity range of that indicated above such as ketones (e.g. methyl isobutyl ketone) and esters (e.g. ethyl acetate) are preferred since they are found to be more selective than alcohols but polar enough to give good distribution characteristics. The most preferred water-immiscible solvents are methyl isobutyl ketone and ethyl acetate. Extraction is conveniently done either under weakly acidic conditions, e.g. pH 4.0–5.0 effected by addition of a mineral acid such as HCl or $H_2SO_4$, or under weakly alkaline broth pH conditions, e.g. pH 8–8.5. Maximum yields have been obtained at pH 4.5–5.0 with methyl isobutyl ketone. Filter aid is preferably added to the extraction mixture and the mixture then filtered. The organic phase is concentrated and diluted with an appropriate antisolvent (non-solvent for the complex) to precipitate out the figaroic acid complex. Suitable antisolvents can be determined by a simple test and include such organic non-solvents for the complex as diethyl ether, benzene and liquid aliphatic hydrocarbons such as n-hexane, n-heptane or Skellysolve B (isomeric hexanes). The preferred antisolvents are diethyl ether and n-hexane. If recovered under alkaline conditions, the purple figaroic acid complex may be converted to the red-orange free acid form by dissolving the complex in water and acidifying the solution to precipitate out the acid form of the complex which can then be recovered by filtration or extracted into organic solvents.

PROPERTIES OF FIGAROIC ACID COMPLEX

The antibiotic complex designated herein as figaroic acid complex is an orange-red amorphous solid in the free acid state. It is insoluble in relatively non-polar solvents such as diethyl ether, benzene and aliphatic hydrocarbons (e.g. n-hexane or n-heptane), mostly soluble in lower alcohols (i.e. $C_1$–$C_8$ alcohols such as methanol, ethanol, n-butanol or 2-propanol), acetone, tetrahydrofuran and dioxane, and totally soluble only in very polar solvents such as dimethylformamide and dimethylacetamide. Upon recovery under alkaline conditions, the complex is deep purple in color indicating conversion of the acid form to the anionic state.

Figaroic acid complex readily forms salts with organic and inorganic bases and pharmaceutically acceptable salts of the complex with such bases are included within the scope of the present invention. Examples of suitable pharmaceutically acceptable salts will be obvious to those skilled in the art and include those salts commonly employed in pharmacy with acidic drugs. The salts are readily obtained by reacting the complex with the appropriate organic or inorganic base. Illustrative of the salts which may be formed are metal salts such as zinc, aluminum, alkali metal (sodium or potassium) or alkaline earth metal (calcium, magnesium or barium), ammonium and organic amine salts such as ethanolamine, ethylenediamine, diethanolamine, procaine or triethanolamine.

The complex contains the elements carbon, hydrogen, oxygen and nitrogen in the following percentages by weight: carbon 53.82%, hydrogen 5.85%, nitrogen 1.63% and oxygen (by difference) 38.70%. It is soluble in aqueous $NaHCO_3$ and $Ba(OH)_2$ giving respectively red-violet and blue solutions. It gives a deep red solution having red fluorescence with alcoholic magnesium acetate and a black solution (orange brown with violet fluorescence on dilution) with alcoholic ferric chloride. The complex gives a positive Tollens test but carbazole and ninhydrin tests are masked by the color of the pigment. It gives no color change with acid zinc dust, sodium bisulfite and hydrogen peroxide. There is a slight fading of the color from violet to red with alkaline sodium bisulfite. Alkaline hydrogen peroxide gives no effect except in large excess whereupon the color fades from violet to pink.

Thin layer chromatograms were run on TLC plates precoated with Silica Gel 60F-254 (Brinkmann). Samples of the complex were made up at concentrations of 2 mg./ml. in chloroform and 40 $\mu$l (80 $\mu$g) portions then applied to the plates. Chromatography was run in tanks having the walls loosely lined with filter paper presaturated with the particular solvent system used. Results (pigment zones were detected visually) were as shown below for the three systems deemed definative. $R_f$ values and (in parentheses) zone intensities, qualitatively estimated as strong (s), moderate (m) and weak (w), are indicated. Zones with an $R_f$ of 0.0 are at the point of application.

System A: chloroform: methanol (19.1) 9 zones noted: $R_f$'s=0.0 (s), 0.39 (w), 0.214 (m), 0.243 (w), 0.349 (m), 0.470 (w), 0.612 (s), 0.651 (s) and 0.694 (m).

System B: chloroform: methanol: formic acid (90:10:1) 14 zones noted: $R_f$'s=0.0 (w), 0.043 (s), 0.073 (m), 0.149 (s), 0.169 (s), 0.212 (w), 0.272 (m), 0.308 (m), 0.368 (w), 0.467 (m), 0.523 (m), 0.722 (s), 0.795 (w) and 0.825 (s).

System C: chloroform: methanol: formic acid (80:20:1) 13 zones noted: $R_f$'s=0.0 (very weak), 0.200 (m), 0.233 (w), 0.279 (m), 0.311 (w), 0.446 (m), 0.472 (s), 0.508 (m), 0.622 (w), 0.741 (m), 0.839 (s), 0.892 (m) and 0.928 (s)."

Figure 1:
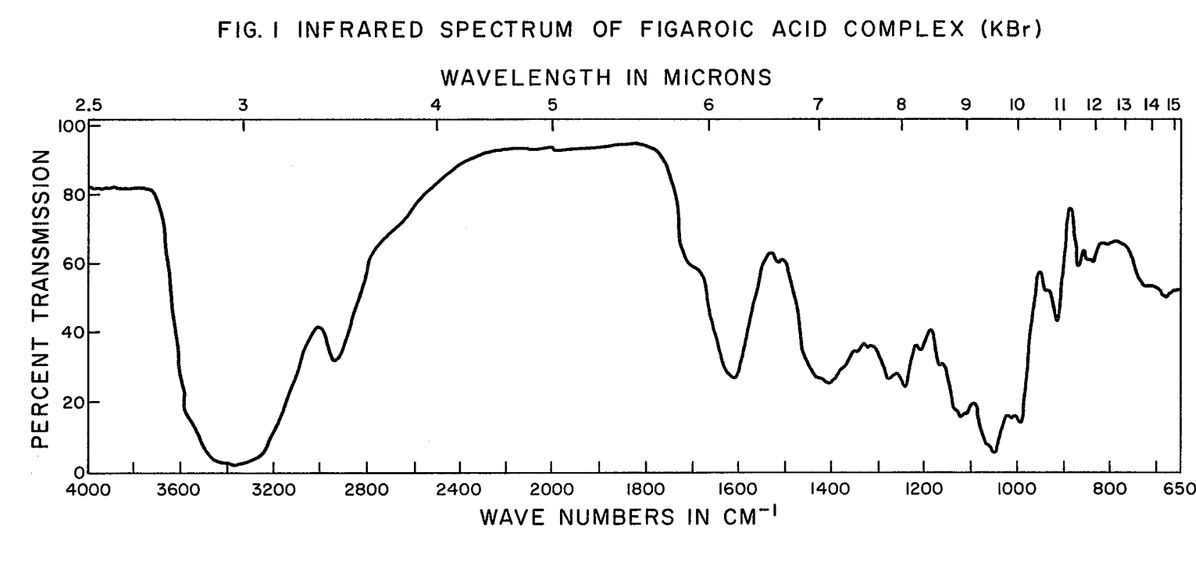
FIG. 1 shows the infra-red absorption spectrum of figaroic acid complex (KBr pellet).
Figure 2:
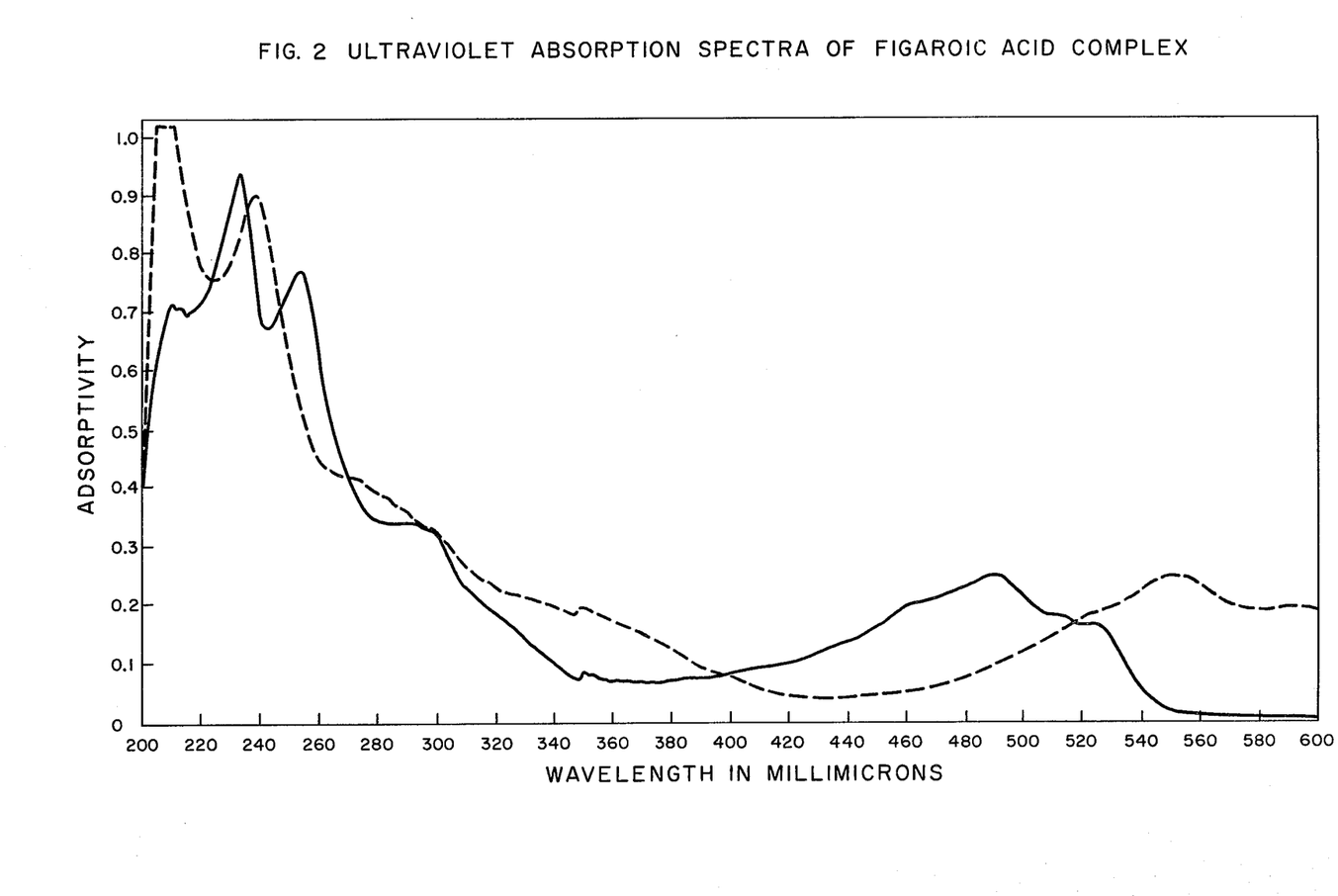
FIG. 2 shows the ultraviolet absorption spectra of figaroic acid complex in 0.1N HCl in methanol (solid line) and in 0.1N NaOH in methanol (dotted line).

The infra-red and ultraviolet absorption spectra of figaroic acid complex indicate that the complex is a mixture of anthracycline components. The infra-red spectrum (KBr pellet) of FIG. 1 shows major bands at 2.94 (broad), 3.4, 6.04–6.13, 6.18, 6.3, 6.95 (broad), 7.1 (broad), 8.1, 9.3, 9.5 and 9.7 $\mu$. The ultraviolet absorption spectra of the complex under acidic and basic conditions are shown in FIG. 2. Adsorptivity in FIG. 2 is defined by the equation $$a = \frac{A}{bc}$$

where A is the adsorbance, b is the cell width in cm. and c is the sample concentration in g./l. At a concentration of 50 $\mu$g./ml. in the 0.1N HCl in methanol, figaroic acid complex shows absorption peaks (solid line) at 233, 253, 287–288 (shoulder), 467 (shoulder), 480 (shoulder), 490, 511 (shoulder) and 524 (shoulder) m$\mu$. In 0.1N NaOH in methanol the complex shows absorption peaks (dotted line) at 238, 266–268 (shoulder) and 553 m$\mu$.

One of the anthracycline components comprising the figaroic acid complex of the present invention has been determined to be carminomycin I previously disclosed by M. G. Brazhnikova, et al. in J. Antibiotics, 27, 254 (1974) as being prepared by fermentation of a species of *Actinomadura*, i.e. *Actinomadura carminata* (See also W. German OLS 2,362,707). Carminomycin has been reported to show promising antitumor activity in a variety of animal and human cancers[see, for example, Cancer Chemother. Rep., Part 1, 58, 255 (1974)].

Carminomycin I may be prepared according to the present invention by mild acid hydrolysis of figaroic acid complex. Thus, the figaroic acid complex may be extracted into an organic solvent, preferably methanol or a mixture of methanol and chloroform, and the organic extract then subjected to mild acid hydrolysis to form carminomycin I which can subsequently be recovered as by evaporation and purified, e.g. by chromatography over Sephadex LH-20. A detailed description of the conversion of figaroic acid complex to carminomycin I is provided in Examples 11–14 below.

leukemia and B-16 melanoma in rodents. Solid figaroic acid complex was also tested and found active on various tumor systems. Results on L-1210 leukemia and B-16 melanoma in mice are shown in Table 5.

Table 5

| | Effect of figaroic acid complex on transplanted mouse tumors | | | | | |
|---|---|---|---|---|---|---|
| | L-1210 leukemia | | | B 16 melanoma | | |
| Dose ug/kg/day | Avg. Wt difference (T-C,g) | T/C percent MST | Survivor Day 5 | Avg. Wt difference (T-C,g) | T/C percent MST | Survivors Day 5 |
| 128 | −5.2 | Tox | 1/6 | −3.4 | Tox | 6/6 |
| 64 | | | | 0 | Tox | 6/6 |
| 32 | −2.8 | 150 | 6/6 | −3.4 | 254[1] | 6/6 |
| 16 | | | | −3.7 | >400[2] | 6/6 |
| 8 | −2.6 | 129 | 6/6 | −0.9 | 206 | 6/6 |
| 4 | | | | +3.6 | 160 | 6/6 |
| 2 | −0.7 | 114 | 6/6 | +0.9 | 126 | 6/6 |
| 1 | | | | −1.7 | 129 | 6/6 |

Treatment:
Once daily for 9 days, intraperitoneally
Evaluation:
T/C percent MST = median survival time in days: Treated MST/Control MST × 100.
Criteria:
T/C ≧ 125 considered significant tumor inhibition (prolongation of host survival)
[1] 2/6 survivors at 60 days
[2] 4/6 survivors at 60 days

BIOLOGICAL ACTIVITY DATA

The in vitro minimum inhibitory concentrations (MIC) of figaroic acid complex were determined for a number of microorganisms using the standard tube dilution procedure. The results shown in Table 4 indicate that several gram-positive organisms, yeast and three protozoans were sensitive to the antibiotic. Gram-negative organisms were insensitive.

Table 4

| Antimicrobial Spectrum of Figaroic Acid Complex | | |
|---|---|---|
| Test organism | | MIC,μg/ml |
| Bacteria: | | |
| Staphylococcus aureus | A9537 | 1.6 |
| Mycobacterium tuberculosis BCG | A9579 | 25 |
| Escherichia coli | A15119 | 50 |
| Pseudomonas aeruginosa | A9843 | >50 |
| Proteus mirabilis | A9900 | >50 |
| Salmonella enteritidis | A9531 | >50 |
| Yeasts: | | |
| Candida albicans | A9540 | 50 |
| Trychophyton mentagrophytes | A9870 | >50 |
| Microsporum canis | A9872 | >50 |
| Protozoa: | | |
| Histoplasma capsulatum | A15056 | 6.3 |
| Trichomonas vaginalis | A22074 | 1.25 |
| Trichomonas faetus | A22075 | 0.31 |

Figaroic acid complex was tested for its ability to induce bacteriophage production in the lysogenic strain of *Escherichia coli* W 1709. Significant induction was observed down to 0.8 μg/ml. Tube dilution protein tests to determine cytoxic effects on He La cells in tissue culture gave a 50% end-point ($ED_{50}$) of 0.004 μg/ml (method described in Antimicrobial Agents and Chemotheropy; 1966: 613–618, 1967).

The effect of figaroic acid complex on several rodent tumor systems was also studied. Details of the method used have been described in Cancer Research 22: 167–173, 1962 and Cancer Chemoth. Reports 3: 1–87– (Part 3), 1972. Treatment of mice having Sarcoma 180 implanted subcutaneously as a solid tumer with figaroic acid complex fermentation broth caused 37% inhibition of tumor diameter increase (estimated 75% inhibition in tumor weight increase). Treatment with the same broth also increased the life span of mice bearing L-1210 leukemia by 29% over control animals. The figaroic acid complex broth was found to be active against Walker 256 carcinosarcoma (intramuscular), P-388 lymphatic leukemia and B-16 melanoma in rodents. Solid figaroic acid complex was also tested and found active on various tumor systems. Results on L-1210 leukemia and B-16 melanoma in mice are shown in Table 5.

The following examples serve to illustrate the invention without limiting it. Skellysolve B is a commercially available petroleum solvent (Skelly Oil Co.) comprising isomeric hexanes and having a b.p. of 60°–68° C. The main component of Skellysolve B is n-hexane. MIBK is methyl isobutyl ketone.

EXAMPLE 1

Shake-flask fermentation

The organism *Streptosporangium* sp. strain C-31,751 is grown on an agar slant medium consisting of 2 g. D-glucose, 20 g. oatmeal, 2 g. soy peptone and 20 g. agar made up to one liter with distilled water. After at least 6 days growth at 27° C., spores are transferred to a 500 ml. Erlenmeyer flask containing 100 ml. of sterile medium consisting of 50 g. corn starch, 10 g. soy flour, 10 g. peanut meal and 3 g. $CaCO_3$ made up to one liter with distilled water. Thus vegetative culture is incubated at 27° C. on a rotary shaker (Gyrotory tier shaker, Model G53, New Brunswick Scientific Co., Inc.) set at 210 rev./min. describing a circle with a 5.1 cm. diameter. After 48 hours 4 ml of culture is transferred to a 500 ml. Erlenmeyer flask containing 100 ml of sterile production medium consisting of 50 g. sucrose, 20 g. soy flour, 20 g. peanut meal and 3 g. $CaCO_3$ made up to one liter with distilled water. The culture is incubated at 27° C. on a shaker set at 230 rev./min. for 170 hours. At this time antibiotic activity consisting of the figaroic acid complex is found in the culture filtrate and mycelium.

EXAMPLE 2

Tank Fermentation

A tank fermentor with 37.8 liters of sterile production medium (as in Example 1) is inoculated with 1.89 liters of vegetative culture prepared according to Example 1, agitated with an impeller speed of 375 rev./min., aerated at a rate of 76.5 liters/min. and incubated at 27° C. After 190 hours the antibiotic complex is isolated.

EXAMPLE 3

Tank fermentation

A tank fermentor with 3030 liters of production medium (as in Example 1) is inoculated with 152 liters of vegetative culture (as prepared by Example 1), agitated with an impeller speed of 155 rev./min., aerated at a rate of 1420 liters/min. and incubated at 27° C. The figaroic acid complex is isolated after 210 hours

EXAMPLE 4

Extraction of Broth and Mycelia at broth pH (slightly alkaline) with n-butanol

Filtration of a broth from a shake flask fermentation using a total of 5 liters of starting medium gave 2.5 liters filtrate, pH 8.5. Of this 1.5 liters was extracted two times with 1 liter batches of n-butanol, the phases separated, and the combined organic phases concentrated. Dilution of the concentrate with diethyl ether gave 1.4 g. of an amorphous purple solid, active against L-1210 leukemia in mice at 2 mg./kg./day. The mycelial cake from broth filtration was stirred for 30 min. with enough methanol to obtain a fluid slurry and then filtered. The filtrate was concentrated until most of the alcohol had been removed and the aqueous residue extracted as above to afford 6.35 g. of figaroic acid complex. The product, an amorphous purple solid, was found to be active vs. L-1210 leukemia in mice at a concentration of 8 mg./kg./day.

EXAMPLE 5

Extraction of whole broth at broth pH with n-butanol

Whole broth, 1.5 liters at pH 8.6, was stirred with about an equal volume of n-butanol. The thick mass was filtered through a Celite (trademark of diatomaceous earth produced by Johns-Manville Products Co.) cake, the phases separated, and the organic phase concentrated to a small volume. This was diluted with excess diethyl ether to precipitate 621 mg of figaroic acid complex. The amorphous purple solid is found to be active against L-1210 leukemia in mice at a dosage of 0.2 mg./kg./day. The solid does not melt but decomposes above 200° C.

EXAMPLE 6

Extraction of whole broth at acid pH with n-butanol

The general procedure of Example 5 was repeated except that pH of the whole broth was adjusted to pH 4.0 with HCl and maintained there during extraction. Four liters of whole broth yielded 1.7 g. of figaroic acid complex in the free acid state as an orange-red solid. The solid is toxic to mice at a concentration of 0.25 mg/kg/day and shows phage inducing properties down to a dilution of 1.5 µg./ml.

EXAMPLE 7

Extraction of whole broth (slightly alkaline) with n-butanol on a large scale

Whole broth (2788 liters at pH 8.6) was stirred with 1357 liters n-butanol. The organic phase was separated to give 783 liters of rich extract which was concentrated to 13 liters. Addition of 80 liters "Skellysolve B" gave 728 g. of the crude purple figaroic acid complex.

EXAMPLE 8

Acid extraction of whole broth with methyl isobutyl ketone (MIBK)

Whole broth (10 liters) which had been stored frozen was thawed and stirred with 10 liters MIBK for 20 minutes after adjustment of the pH to 4.5. Filter aid was stirred into the mixture and the latter was then filtered on a filter aid pad. The phases in the filtrate were separated and the organic phase concentrated to a small volume. Dilution of this with excess "Skellysolve B" gave 4 g. of the orange-red figaroic acid complex free acid having phage inducing activity at a dilution of 6.2 µg/ml.

EXAMPLE 9

Acid extraction of whole broth with methyl isobutyl ketone on a large scale (MIBK)

Whole broth (3095 liters) was adjusted from pH 8.35 to 3.35 at 10° C. by addition of 49 liters 30% $H_2SO_4$ with stirring and cooling. Two volumes (6412 liters) MIBK were stirred with the broth followed by addition of excess filter aid (diatomaceous earth). The mixture was filtered across a precoated vacuum filter using 2554 liters additional MIBK as rinse. The rich MIBK extract (7555 liters) was separated and concentrated to 10 liters. During the concentration 1.285 kg. of wet solids precipitated and were collected. Addition of 100 liters "Skellysolve B" to the concentrate afforded an additional 365 g. of crude oily material. The first crop of solids was dried to 858 g. and divided into three batches. Each of these was stirred in 4 liters acetone and insoluble matter filtered off. The latter proved to be filter aid and, when combined and dried, weighed 367 g. The acetone solution was concentrated and diluted with excess diethyl ether to give 294.5 g. of crude figaroic acid complex. Evaporation of the ether gave 19.2 g. of inactive material. The oily "Skellysolve B" precipitate was treated also with diethyl ether, but proved inactive.

EXAMPLE 10

Conversion of figaroic acid complex salt to its free acid form

The crude purple solid (25 g.) obtained by alkaline n-butanol extraction as described in Example 7 was stirred in 1 liter $H_2O$ at 25° until it dissolved. The purple solution was adjusted downward in pH from 8.3 to 1.1 by dropwise addition of concentrated HCl with stirring. Figaroic acid complex free acid formed as a fine, silt-like brick-red precipitate and was collected by centrifugation. After drying it weighed 13.6 g. and was active against the L-1210 tumor system in mice down to 0.2 mg./kg./day dosage. The supernatant liquor was lyophilized to yield 10.0 g. of totally inactive amorphous solids containing 7.8% ash by ignition. The results of the combustion analysis indicate that the cationic material bound to the purple anionic figaroic acid complex is largely organic.

EXAMPLE 11

Conversion of Figaroic Acid Complex to Carminomycin I

A suspension of figaroic acid complex (100 g.) in 500 ml. of methanol: chloroform (4:1) was stirred 10 min. and then filtered. The filter cake was washed three times with 100 ml. portions of methanol. The filtrate and washings were reduced to a volume of 500 ml. at reduced pressure. To this solution was added 10 ml. concentrated HCl with stirring. The solution was stirred 30 min. at 23° C. and then poured into 3 liters of chloroform. Distilled water (4 liters) was added to the solution and formation of a precipitate was observed. The resulting suspension was shaken, filtered and the layers separated. The organic layer was dried over $Na_2SO_4$ and evaporated. The aqueous layer was adjusted to pH 7-8 with $NaHCO_3$ and extracted with 5 × 500 ml. of chloroform. The chloroform extracts were dried over $Na_2SO_4$ and evaporated to yield 1.515 g. of a solid which was shown by thin layer chromatography (silica gel plates - *LQD from Quanta/Gram using a developing system of chloroform: methanol; formic acid - 85:15:1) to consist primarily of carminomycin I by comparison with an authentic sample. Similarly, high pressure liquid chromatography indicated the sample to be largely carminomycin I.

* Manufactured by Quantum Industries 341 Kaplan Drive Fairfield, New Jersey

EXAMPLE 12

Preparation of Carminomycin I from Figaroic Acid Complex

A. Preparation of Partially Purified Figaroic Acid Complex

Figaroic acid complex (400 g.) was stirred with 2500 ml. water for 15 min. and then filtered. The procedure was repeated and the filtrates then combined. The filter cake was stirred with 2500 ml. methanol for 15 minutes and filtered. The cake was washed with 2500 ml. methanol and the combined filtrate evaporated to give 42.7 g. of a solid shown by bioassay to contain from 50-70% of the total bioactivity in the original figaroic acid complex sample (hereinafter referred to as solid "A"). The filter cake was washed with chloroform until it was colorless, and the combined filtrate was evaporated to yield 16.4 g. of a solid (solid "B"). Thin layer chromatography of solid "A" indicated the presence of a substantial amount of $\epsilon$-rhodomycinone impurity in the sample. Solid "A" was suspended in 100 ml. of chloroform for 10 minutes and filtered. This procedure was repeated six times. Evaporation of the chloroform filtrate gave 20 g. of a solid rich in $\epsilon$-rhodomycinone. The solids from the filtration step were combined (8 g. total solids) and shown by high pressure liquid chromatography to be partially purified figaroic acid complex (low in $\epsilon$-rhodomycinone impurity).

B. Hydrolysis of Figaroic Acid Complex to Carminomycin I

To 1.0 g. of the partially purified figaroic acid complex prepared in Step A above in 50 ml. of methanol: chloroform (9:1) was added 1 ml. of concentrated hydrochloric acid. After letting the solution stand for 90 min. at 23° C., crude carminomycin I (0.185 g.) was recovered following the procedure of Example 11.

The above hydrolysis procedure in Step B was scaled up using 2 g. of figaroic acid complex and a hydrolysis period of 30 min. The yield of carminomycin I was 0.370 g.

EXAMPLE 13

Preparation of Carminomycin I Hydrochloride

To a solution of carminomycin I (prepared according to Example 12) in 10 ml. chloroform and 2 ml. methanol was added 2 ml. of 5% methanolic hydrochloric acid. The solution was allowed to stand for 1 min. and 25 ml. diethyl ether then added. The solution was filtered to yield 0.885 g. of crude carminomycin I hydrochloride. A 100 mg. sample of the crude solid was dissolved in 20 ml. water and extracted three times with ethyl acetate. The aqueous phase was lyophilized to yield 85 mg. of carminomycin I hydrochloride.

EXAMPLE 14

Purification of Carminomycin I

A solution of crude carminomycin I (1 g.) in 20 ml. of methanol: chloroform (1:1) was layered onto a column of Sephadex LH-20 (700 g. dry weight swollen with chloroform - column dimensions 5 cm. × 170 cm. - bed height = 130 cm.). Chloroform was passed through the column at the rate of 8 ml./min. After four hours the flow rate was slowed to 4.6 ml./min. and the eluant collected using a fraction collector (9.2 ml. fractions taken every 2 min.). A total of 500 fractions were taken. The cuts were made as indicated in the table below.

| Sephadex LH-20 Chromatography of Crude Carminomycin I | | |
|---|---|---|
| Fraction No. | Tubes | Wt.(mg.) |
| 1 | 1-40 | 175.6 |
| 2 | 41-46 | 21.9 |
| 3 | 47-61 | 84.9 |
| 4 | 62-70 | 12.8 |
| 5 | 71-86 | 30.6 |
| 6 | 87-94 | 6.2 |
| 7 | 95-106 | 16.3 |
| 8 | 107-116 | 16.7 |
| 9 | 117-130 | 17.3 |
| 10 | 131-144 | 40.2 |
| 11 | 145-150 | 50.4 |
| 12 | 151-158 | 36.5 |
| 13 | 159-171 | 194.4 |
| 14 | 172-180 | 25.7 |
| 15 | 181-200 | 38.1 |
| 16 | 201-240 | 36.1 |
| 17 | 241-324 | 43.0 |
| 18 | 325-420 | 60.7 |
| 19 | 420-500 | 26.4 |

Fraction No. 13 proved to be pure carminomycin I by use of NMR chromatography and biassay (ILB, BS-8 and L1210).

We claim:

1. A process for producing the antibiotic complex designated figaroic acid complex which comprises cultivating a figaroic acid-producing strain of Streptosporangium having the charactertistics of A.T.C.C. 31129 in an aqueous nutrient medium containing assimilable sources of nitrogen and carbon under submerged aerobic conditions until a substantial amount of figaroic acid complex is produced by said organism in said culture medium.

2. The process of claim 1 which includes the further step of recovering the figaroic acid complex from the culture medium.

3. The process of claim 2 wherein the whole cultural broth is extracted with a $C_4$-$C_8$ alcohol, methyl isobutyl ketone, methylene chloride or ethyl acetate, the organic phase concentrated, and the solid figaroic acid complex precipitated by dilution of the concentrated organic extract with diethyl ether, benzene, n-hexane, n-heptane or isomeric hexanes.

4. The process of claim 3 wherein the whole broth is extracted with n-butanol and the solid complex precipitated from the concentrated organic extract with diethyl ether or n-hexane.

5. The process of claim 2 wherein the whole broth is adjusted with acid to a pH of about 4.5-5.0, the broth is extracted with methyl isobutyl ketone, the organic phase is concentrated, and the solid figaroic acid complex is precipitated by dilution of the concentrated organic extract with diethyl ether or n-hexane.

6. The anthracycline anitbiotic complex, figaroic acid complex, or a pharmaceutically acceptable salt thereof, which antibiotic complex has the following characteristics:

(a) it is an orange-red amorphous solid in the free acid state and an amorphous deep purple solid when recovered under alkaline conditions;
(b) it is soluble in dimethylformamide and dimethylacetamide, mostly soluble in lower alcohols, acetone, tetrahydrofuran and dioxane and insoluble in diethyl ether, benzene and aliphatic hydrocarbons;
(c) it is capable of forming salts with bases;
(d) it is soluble in aqueous $NaHCO_3$ and $Ba(OH)_2$ giving, respectively, red-violet and blue solutions;
(e) it gives a deep red solution having red fluorescence with alocoholic magnesium acetate and a black solution with alcoholic ferric chloride;
(f) it gives a positive Tollens test;
(g) it gives no color change with acidic zinc dust, acidic sodium bisulfite or acidic hydrogen peroxide;
(h) it shows a slight fading of color with alkaline zinc dust from violet to red, a rapid change in color from violet to red with alkaline sodium bisulfite and no color change with alkaline hydrogen peroxide except in large excess whereupon the color fades from violet to pink;
(i) it has an infrared spectrum when pelleted in potassium bromide substantially as shown in FIG. 1;
(j) it has ultraviolet absorption spectra when dissolved in 0.1 HCl in methanol and 0.1N NaOH in methanol, respectively, at a concentration of 50 μg/ml. substantially as shown in FIG. 2;
(k) it is effective in inhibiting the growth of various Gram-positive bacteria, protozoa and yeasts;
(l) it is effective in inhibiting the growth of Sarcoma 180, L-1210 lymphatic leukemia, Walker 256 carcinosarcoma, P-388 lymphatic leukemia and B-16 melanoma tumor systems in rodents;
(m) it exhibits phage inducing properties;
(n) it contains the elements carbon, hydrogen, oxygen and nitrogen in substantially the following percentages by weight: carbon 53.82%, hydrogen 5.85%, nitrogen 1.63% and oxygen (by difference) 38.70%; an
(o) it exhibits the following $R_f$ values as determined by silica gel thin layer chromatography:
  1. in the solvent system chloroform: methanol (19:1) — $R_f$'s of 0.0, 0.39, 0.214, 0.243, 0.349, 0.470, 0.612, 0.651 and 0.694.
  2. in the solvent system chloroform: methanol: formic acid (90:10:1) — $R_f$'s of 0.0, 0.043, 0.73, 0.149, 0.169, 0.212, 0.272, 0.308, 0.368, 0.467, 0.523, 0.722, 0.795 and 0.825; and
  3. in the solvent system chloroform: methanol: formic acid (80:20:1) — $R_f$'s of 0.0, 0.200, 0.233, 0.279, 0.311, 0.446, 0.472, 0.508, 0.622, 0.741, 0.839, 0.892 and 0.928.

* * * * *